United States Patent [19]

Gaillard

[11] Patent Number: 5,437,679
[45] Date of Patent: Aug. 1, 1995

[54] NAIL SPLITTER DEVICE FOR IMPLEMENTING A WEDGE RESECTION PROCEDURE TO REMOVE AN INGROWN TOENAIL

[76] Inventor: Douglas S. Gaillard, 2820 Hazelwood Dr., No. B-8, Nashville, Tenn. 37212

[21] Appl. No.: 251,390

[22] Filed: May 31, 1994

[51] Int. Cl.⁶ ............................................. A45D 29/02
[52] U.S. Cl. ....................................... 606/131; 30/28; 30/179; 132/75.5
[58] Field of Search ................... 606/1, 167, 131, 172, 606/174, 175, 190, 205–211; 30/26–29, 145, 146, 179, 191, 193, 178, 123, 123.5, 123.7, 131–135, 142, 152, 155, 173, 175, 176, 186; D28/60; 132/75.5, 75.4, 75.3, 73

[56] References Cited

U.S. PATENT DOCUMENTS

| | | | |
|---|---|---|---|
| D. 326,165 | 5/1992 | Leine | D28/60 |
| 327,065 | 9/1885 | Burton | 132/75.6 |
| 528,317 | 10/1894 | Bailey | 606/131 |
| 1,976,067 | 10/1934 | Manson | D28/60 |
| 2,507,345 | 5/1950 | Meesook | 30/28 |
| 2,521,027 | 9/1950 | Sorenson | 30/28 |
| 2,839,827 | 6/1958 | David | 30/28 |
| 3,315,354 | 4/1967 | Oates, Jr. | D28/60 |
| 3,430,340 | 3/1969 | Perles | 30/28 |
| 3,844,032 | 10/1974 | Siegal | 30/193 |
| 3,981,298 | 9/1976 | Vironda | 602/31 |
| 4,936,322 | 6/1990 | DeSantis | 132/75.6 |
| 4,964,213 | 12/1990 | Suggs | 132/75.5 |
| 5,101,563 | 4/1992 | d'Orgelys | 30/28 |
| 5,197,961 | 3/1993 | Castle | 606/1 |
| 5,261,872 | 11/1993 | Goldenberg | 602/31 |

Primary Examiner—Stephen C. Pellegrino
Assistant Examiner—Glenn Dawson
Attorney, Agent, or Firm—Waddey & Patterson; I. C. Waddey, Jr.

[57] ABSTRACT

A nail splitter for splitting a ingrown toenail in order to remove the severed portion of the nail from the soft tissue of the digit and allow the nail to grow back flat to prevent further irritation of the soft tissue of the digit. The device is of a scissor or plier type structure having an elongated, flat separator tongue with a rounded tip and a sharp blade connected to the separator tongue by a hinged connection. The blade overlies the flat separator tongue and can be pressured to make a slicing engagement with the upper side of the separator tongue to sever the nail between the separator tongue and the blade. The tip of the blade has a hawk-nosed configuration that overlies the rounded nose of the separator tongue when the blade is pressed into engagement position. The hawk-nosed tip of the blade overlies the rounded nose of the flat depressor tongue so that the structure can be pushed beneath the cuticle of the toe without severing the cuticle to reach the base of the nail and a second cutting action can be performed to sever the portion of the nail beneath the cuticle. Once the entire nail has been separated, the hawk-nosed tip of the blade can be maneuvered to engage the severed portion of the nail to assist in removing it from the soft tissue of the digit.

4 Claims, 5 Drawing Sheets

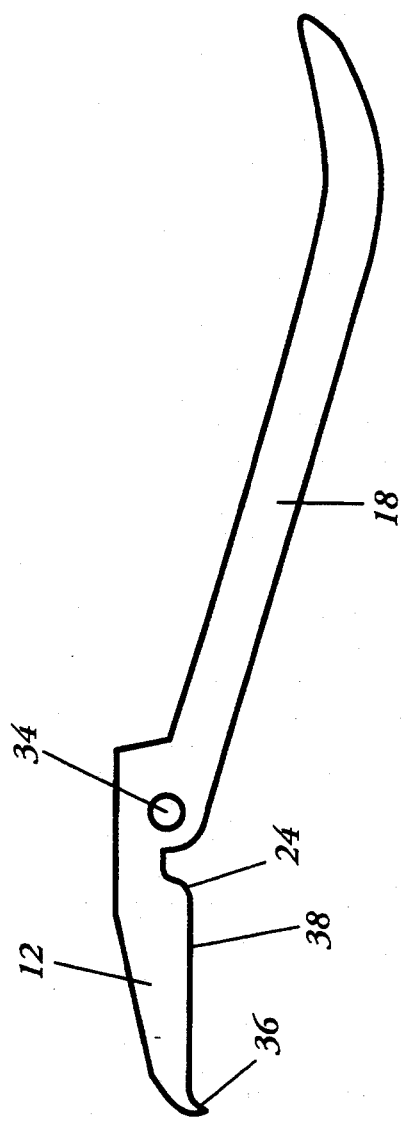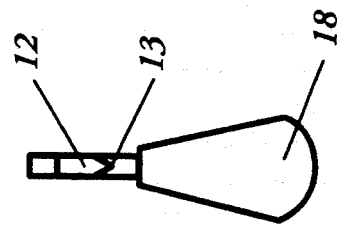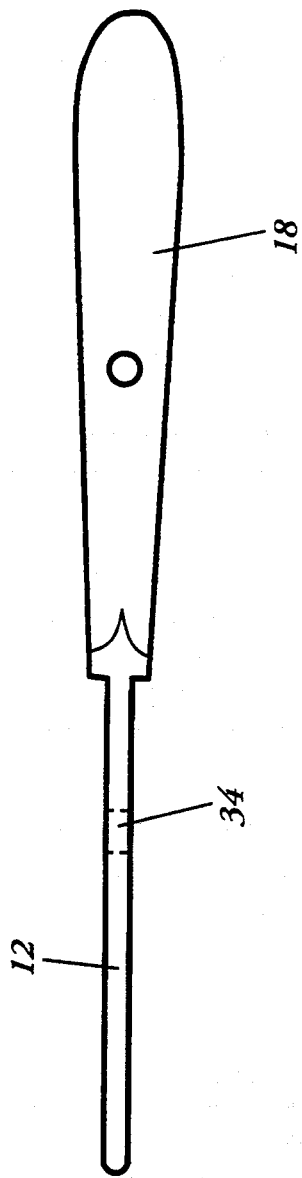
FIG. 8
FIG. 9
FIG. 10

NAIL SPLITTER DEVICE FOR IMPLEMENTING A WEDGE RESECTION PROCEDURE TO REMOVE AN INGROWN TOENAIL

BACKGROUND OF THE INVENTION

The present invention relates generally to a device for use in removing ingrown toenails and more particularly to a nail splitter for implementing a procedure known as a "wedge resection". The device has a plier or scissor type construction, including co-acting jaws used to split a nail in order to remove the ingrown portion of the toenail with minimal intrusive procedure and trauma to the infected area.

It will be appreciated by those skilled in the art that ingrown nails (usually toenails) are a common malady that often must be corrected by an outpatient operative procedure. The phrase "ingrown toenail" is used to describe the condition where the edge of the toenail or fingernail grows into the soft tissue of the digit, causing inflammation, and on occasion an abscess. When an ingrown toenail occurs, the surgical procedure used to correct it to split the nail and remove the portion of the nail that has turned and grown radially into the soft tissue of the digit.

The corrective procedure for ingrown toenails is illustrated in U.S. Pat. No. 4,936,322 issued to DeSantis on Jun. 26, 1990. DeSantis describes the procedure, and in FIGS. 5 and 6 illustrates the procedure of splitting the nail so that the ingrown portion of the nail can be removed. DeSantis' description of the procedure is done in conjunction with the description of his invention for a "Ingrown Toenail Part Remover" which he describes and claims in the referenced patent.

The DeSantis device is a radical departure from the more traditional prior art devices used for this procedure. As DeSantis describes, the prior art devices include pliers and scissor type devices, such devices being by far and away the norm for use in executing this procedure. DeSantis recognizes that prior art safety blades have certain drawbacks. Further, he recognizes that the use of separate depressors to separate the soft tissue of the nail can be awkward to use and may result in unnecessary trauma to the affected region because of multiple insertions of separators, cutting devices, etc.

The object of Applicant's invention is to overcome the deficiencies of the prior art with a more traditional instrument which is an improvement over the instruments with which this procedure is currently undertaken. To that end, Applicant's device is a scissor or plier type instrument having a flat separator tongue with a rounded nose which is hingedly connected to a cutter blade for severing the nail once the separator tongue has been inserted between the nail and the soft tissue.

Another problem that exists with this procedure using traditional instruments is that the nail, which extends approximately 2-3 mm beneath the cuticle must be cut throughout its full length. Prior art devices have traditionally involved cutting the cuticle as well as the nail in order to cut the nail to its base. Cutting the cuticle generates an unnecessary trauma to the region and may result in infection and delays in the healing process. Therefore, another object of Applicant's invention is to provide a device for implementing this procedure which avoids cutting the cuticle while at the same time enabling the device to cut the nail throughout its entire length. To this end, Applicant's cutting device provides a hawk-nose on the tip of the cutter blade which mates with the rounded nose of the separator tongue so that when the blade is pressed against the tongue and the nail as cut, the cut can be made to a point immediately adjacent the cuticle. The blade is then opened slightly so that the hawk-nosed portion of the blade will slide under the cuticle when the device is pushed toward the base of the nail, thereby separating the cuticle from the nail and allowing the blade to cut the base of the nail but avoiding any cut to the cuticle. Once the hawk-nose of the blade is inserted beneath the cuticle and extended to the base of the nail, the blade can be once again pressed against the separator tongue so that the nail can be cut throughout its entire length. The device can then be used to capture the severed portion of the nail because of the overlapping engagement of the hawk-nosed portion of the cutting blade with the separator tongue. When those two elements are engaged about the severed portion of the nail, one can gently remove the severed portion of the nail from the toe. A device providing these features and enabling this procedure to be effectively performed in the fashion described is not currently available in the prior art.

SUMMARY OF THE INVENTION

My invention is of a nail splitter for splitting a ingrown toenail in order to remove the severed portion of the nail from the soft tissue of the digit and allow the nail to grow back flat to prevent further irritation of the soft tissue of the digit. The device is of a scissor or plier type structure having an elongated, flat separator tongue with a rounded tip and a sharp blade connected to the separator tongue by a hinged connection. The blade overlies the flat separator tongue and can be pressured to make a slicing engagement with the upper side of the separator tongue to sever the nail between the separator tongue and the blade. The tip of the blade has a hawk-nosed configuration that overlies the rounded nose of the separator tongue when the blade is pressed into engagement position. The hawk-nosed tip of the blade overlies the rounded nose of the flat depressor tongue so that the structure can be pushed beneath the cuticle of the toe without severing the cuticle to reach the base of the nail and a second cutting action can be performed to sever the portion of the nail beneath the cuticle. Once the entire nail has been separated, the hawk-nosed tip of the blade can be maneuvered to engage the severed portion of the nail to assist in removing it from the soft tissue of the digit.

BRIEF DESCRIPTION OF THE DRAWINGS

FIG. 8 is a side view of the cutter blade and its handle.

FIG. 9 is a top view of the cutter blade and its handle.

FIG. 10 is an end view of the cutter blade and its handle.

DESCRIPTION OF THE PREFERRED EMBODIMENT

The description of the preferred embodiment will be best understood when reference is made to the foregoing drawings wherein the features of the invention are illustrated and like numerals are consistently used throughout the various figures.

Figure 1:
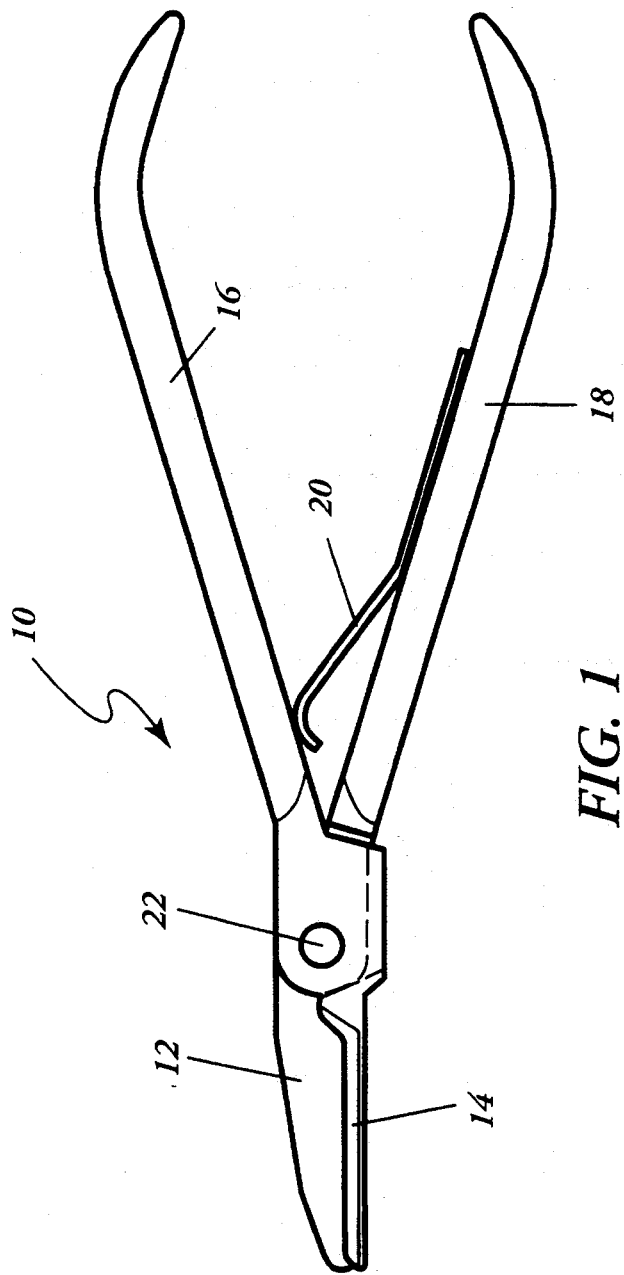
FIG. 1 is an elevation device.
Figure 2:
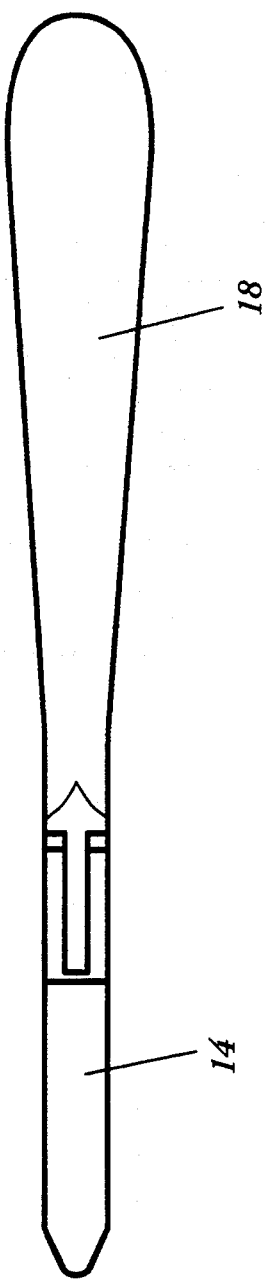
FIG. 2 is a top view of the device.
Figure 3:
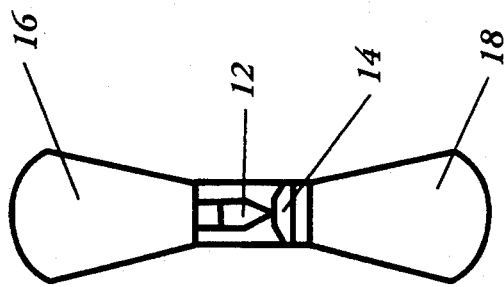
FIG. 3 is an end view of the device.

Referring now to FIG. 1, a side view of the device is illustrated. The nail splitter 10 includes a cutter 12, a separator tongue 14, a stabilizing handle 16 and a pressure handle 18. FIG. 2 shows a bottom view of the assembled nail splitter 10 and FIG. 3 shows an end view of the assembled nail splitter 10 looking from the direction of the cutter 12 and separator tongue 14 toward the stabilizing handle 16 and pressure handle 18.

As can be seen from FIGS. 1, 11, 12 and 14, the nail splitter 10 is of a scissor or plier type construction with the separator tongue 14 hingedly connected to the cutter 12.

Figure 4:
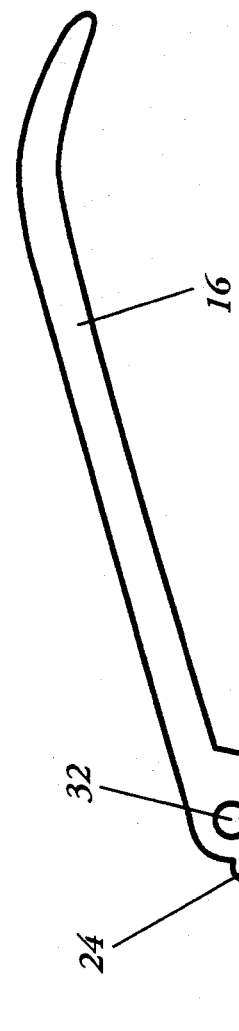
FIG. 4 is a side view of the separator tongue and its handle.

In FIG. 4, there is illustrated the unitary construction of the separator tongue 14 and the stabilizing handle 16. FIGS. 8 and 9 illustrate the unitary construction of cutter 12 with the pressure handle 18. The combination cutter 12/pressure handle 18 has a pivot point 34 which is co-axial with the hole 32 passing through the combination separator tongue 14/stabilizing handle 16 when the nail splitter 10 is assembled. The nail splitter 10 is then hinged by passing a pivot 22 through the hole 32 and pivot point 34. Other similar hinging structures may be employed in order to hingedly connect the combination separator tongue 14/stabilizing handle 16 with the combination cutter 12/pressure handle 18.

Figure 6:
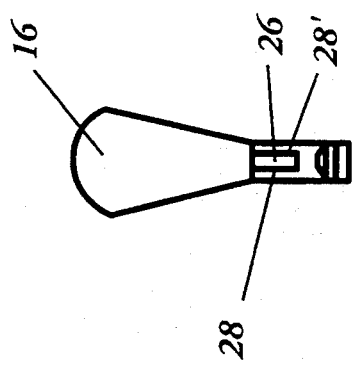
FIG. 6 is an end view of the separator tongue and its handle.
Figure 5:
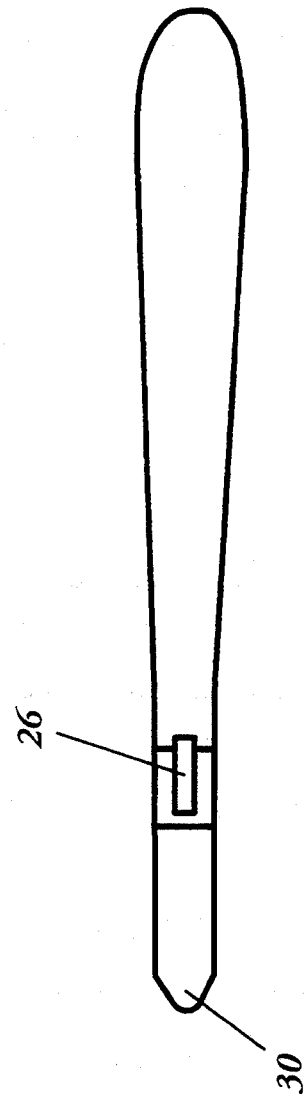
FIG. 5 is the top view of the separator tongue and its handle.

As can be seen from FIGS. 5 and 6, the combination separator tongue 14/stabilizing handle 16 is formed with upwardly extending arms 28, 28' and the cutter 12 has the pivot point 34 passing through it which aligns with the hole 32 passing through the upwardly extending arms 28, 28'.

Figure 11:
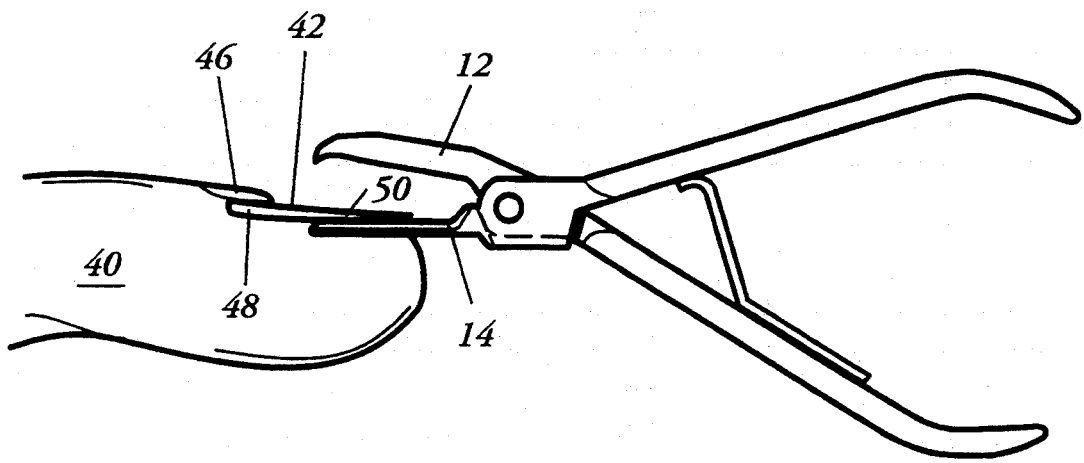
FIG. 11 is a side view of the device in use with the cutter blade opened to allow insertion of the separator tongue beneath the toenail.

Looking at FIGS. 1 and 11, it can be seen that spring 20 is connected to pressure handle 18 and slidably engaged against the underside of the stabilizing handle 16 so that in the standing mode, the nail splitter 10 is pressed to an open position by the bias of the spring (see FIG. 11). When the nail splitter 10 is being used, the stabilizing handle 16 is held in the user's palm with the user's fingers curled about the pressure handle 18. Collapsing pressure is applied on the pressure handle 18 moving it against the bias of the spring 20 toward the stabilizing handle 16 into the closed position shown in both FIGS. 1 and 2. By virtue of the hinged connection of the device about the pivot 22, moving the pressure handle 18 towards the stabilizing handle 16 causes a downward movement of the cutter 12 toward the separator tongue 14.

Referring now to FIGS. 4 and 8, there is shown formed within the combination separator tongue 14/stabilizing handle 16 a shoulder 24. Viewing FIG. 8, there is shown the cam 24' formed in the cutter 12 proximate the point of pivot 22. When the nail splitter 10 is being used, the collapsing pressure applied to pressure handle 18 moving it in the direction of stabilizing handle 16 will tend to force the cutter 12 against the separator tongue 14. However, the cam 24' engages shoulder 24 at a point when the cutting edge 38 is proximate the upper surface of the separator tongue 14 but separated from the upper surface of the separator tongue 14 by approximately 0.001 inches. Thus, the cutting edge 38 will be allowed to perform its cutting function as hereinafter described against an ingrown toenail, but will not come into engagement with the upper surface of the separator tongue 14. Since the nail will be split through substantially all of its thickness, the ingrown portion of the toenail will be easily separated from the balance of the nail; however, the cutting edge of the nail splitter 10 will not be dulled and therefore the instrument can be used repeatedly without having to be resharpened or replaced. Further, sharpening of the cutting edge 38 would be practically impossible because in order to perform the procedure for which this instrument is designed, the plane of the upper surface of lo the separator tongue 14 must remain substantially parallel to the line of the cutting edge 38.

Figure 7:
FIG. 7 is an exploded side view of the tip of the separator tongue.

Referring to FIGS. 5 and 7, the tip of the separator tongue 14 is shown in more detail. The tip of the separator tongue 14 has a bull-nose 30 which is rounded rather than terminating in a sharp, pointed or cutting edge. By constructing the separator tongue 14 in a flat, thin, elongated shape as shown in FIGS. 4 and 5, with the rounded bull-nose 30 at the tip of the separator tongue 14, the separator tongue 14 can be used to separate the toenail from the soft tissue of the toe with minimal trauma to the patient.

As has been indicated, prior art devices having a scissor type construction generally have a sharp, pointed edge which tends to cut the soft tissue beneath the toenail. Use of devices of the type of the prior art often results in substantial traumatization of the area and may lead to further complications. While this procedure is being conducted while the digit is anesthetized, the pain that the patient may suffer later is exaggerated when a vertical cut of the soft tissue occurs. With use of the nail splitter of the present invention, the separator tongue 14 will have a minimal intrusive effect while sliding beneath the toenail and separating the soft tissue from the nail itself. Thus, the patient suffers significantly reduced post-procedure pain and likelihood of complication.

Figure 12:
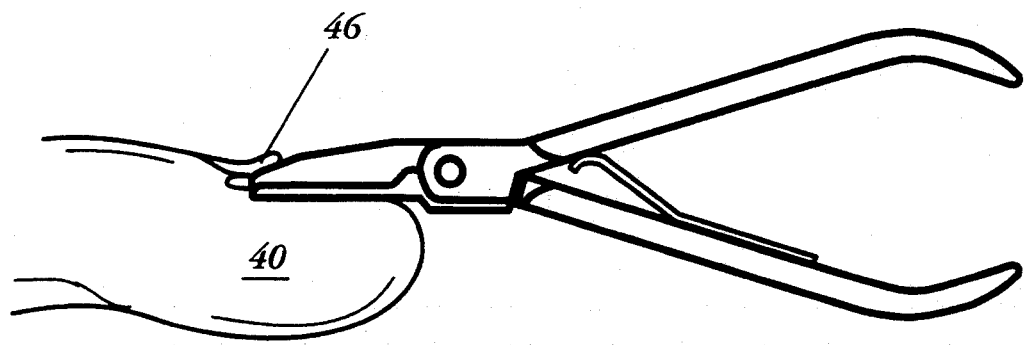
FIG. 12 is a side view of the device in use showing the cutter blade clamped down onto the separator tongue to cut the nail and the nose of the cutter blade pushed beneath the cuticle of the toe.
Figure 13:
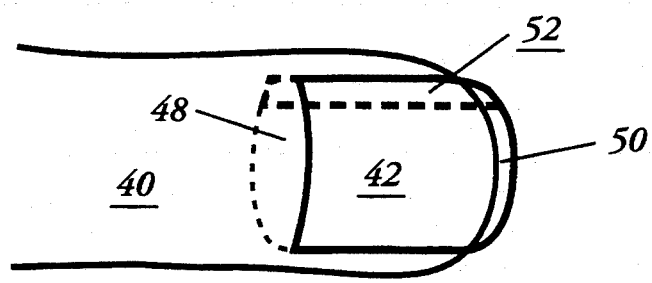
FIG. 13 is a top view of a toe with an ingrown toenail.

FIGS. 11-14 show the device of the present invention in operation. FIG. 13 shows an illustration of a toe and an ingrown toenail. The toe has a nail 42 with base 48 and tip 50. The base 48 is beneath the cuticle 46 and the nail shown in FIG. 13 has an ingrown section 52.

The first step of the procedure using the nail splitter of the present invention is to insert the separator tongue 14 beneath the tip of the nail 50 and to separate the nail 42 from the soft tissue of the toe 40. This initial step of the procedure is shown in FIG. 11. The separator lo tongue, as indicated, has bull-nose 30 and a flat, thin, elongated configuration which allows it to serve as a separator rather than a cutter to separate the nail 42 from the toe 40.

Figure 14:
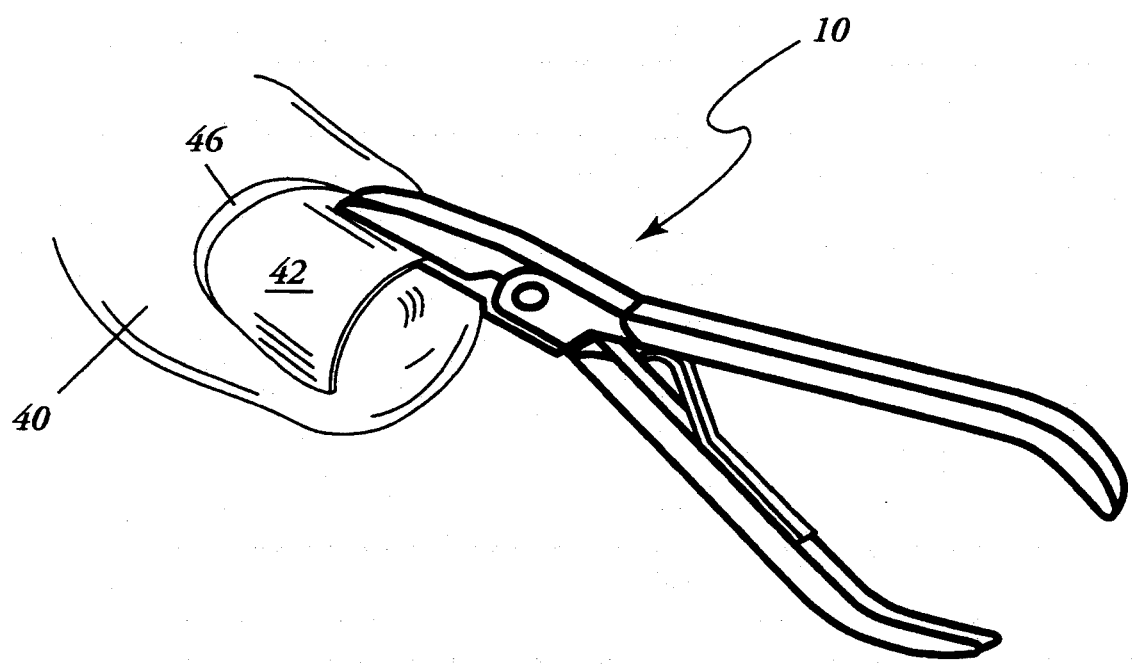
FIG. 14 is a perspective view of the device of the present invention being used in the nail splitter procedure.

Once the nail has been separated from the toe by insertion of the separator tongue 14, the stabilizing handle 16 is held in the palm of the user's hand and pressure is applied by pulling the fingers wrapped around pressure handle 18 toward the palm and causing the cutter 12 to move toward the separator tongue 14 and split the nail as can be seen in FIG. 14. Once the nail is split to approximately the location of the cuticle 46, the hawk-nose 36 (see FIG. 8) of the cutter 12 fits over the bull-nose 30 (as is best illustrated in FIG. 7) of the separator tongue 14. The pressure of the spring 20 is then allowed to create a slight opening of the engagement between the separator tongue 14 and the cutter 12 so as to be separated by the thickness of the nail 42. The hawk-nose 36 of the cutter 12 is then slit along the top of the nail as the separator tongue 14 separates the base of the nail 48 from the toe 40. The hawk-nose 36 of the cutter 12 will slide beneath the cuticle 46 as is seen in FIG. 12 so that the base of the nail can be split without damaging the cuticle. A second action of applying engaging pressure against the pressure handle 18 in the direction of the stabilizing handle 16 is implemented to make the final cut.

After the nail is split throughout its entire length, the hawk-nose 36 of the cutter 12 can be engaged over the ingrown section 52 of the toenail 42 to assist with removal of the split portion of the nail, namely the ingrown section 52. In this procedure, the ingrown section 52 is removed to allow the nail to grow back straight and avoid the traumatization of the area generally experienced by patients with this malady.

By use of the present invention, the wedge resection procedure for which this device is designed can be implemented with minimum traumatization to the area, while reducing the pain associated with the procedure along with the healing period that the patient must experience once the procedure is completed.

Thus, although there have been described particular embodiments of the present invention of a new and useful "Device for Implementing a Wedge Resection Procedure to Remove an Ingrown Toenail", it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. A nail splitter including:
   a) a separator tongue and a cutter;
   b) said separator tongue having a proximal end and a distal end;
   c) said cutter having a proximal end and a distal end;
   d) means hingedly connecting said separator tongue and said cutter at their proximal ends whereby said cutter can be moved between an engaged position and a disengaged position relative to said separator tongue;
   e) said separator tongue having an elongated, thin, flat shape;
   f) the distal end of said separator tongue having a smooth rounded profile;
   g) said separator tongue having an upper planer surface;
   h) said cutter having a cutting edge overlying said separator tongue substantially throughout the length thereof and substantially co-planer with the upper planer surface of the separator tongue when said cutter and said separator tongue are in the engaged position and said cutting edge being at an angle relative to said upper planer surface of said separator tongue when the separator tongue and said cutter are in the disengaged position; and
   i) means for moving the cutter between the engaged position and the disengaged position relative to the separator tongue.

2. The nail splitter of claim 1 wherein the cutter lies in a plane and the plane of the cutter is substantially perpendicular to the upper planer surface of the separator tongue.

3. The nail splitter of claim 1 wherein the distal end of the cutter has a hawk-nose that overlies the rounded profile of the distal end of the separator tongue when said cutter and said separator tongue are in the engaged position.

4. The nail splitter of claim 1 including means limiting the movement of said cutter relative to said separator tongue whereby, when said cutter and said separated tongue are in the engaged position, the cutting edge is approximately 0.001 inches spaced from the upper planer surface of the separator tongue.

* * * * *